Figure 1:
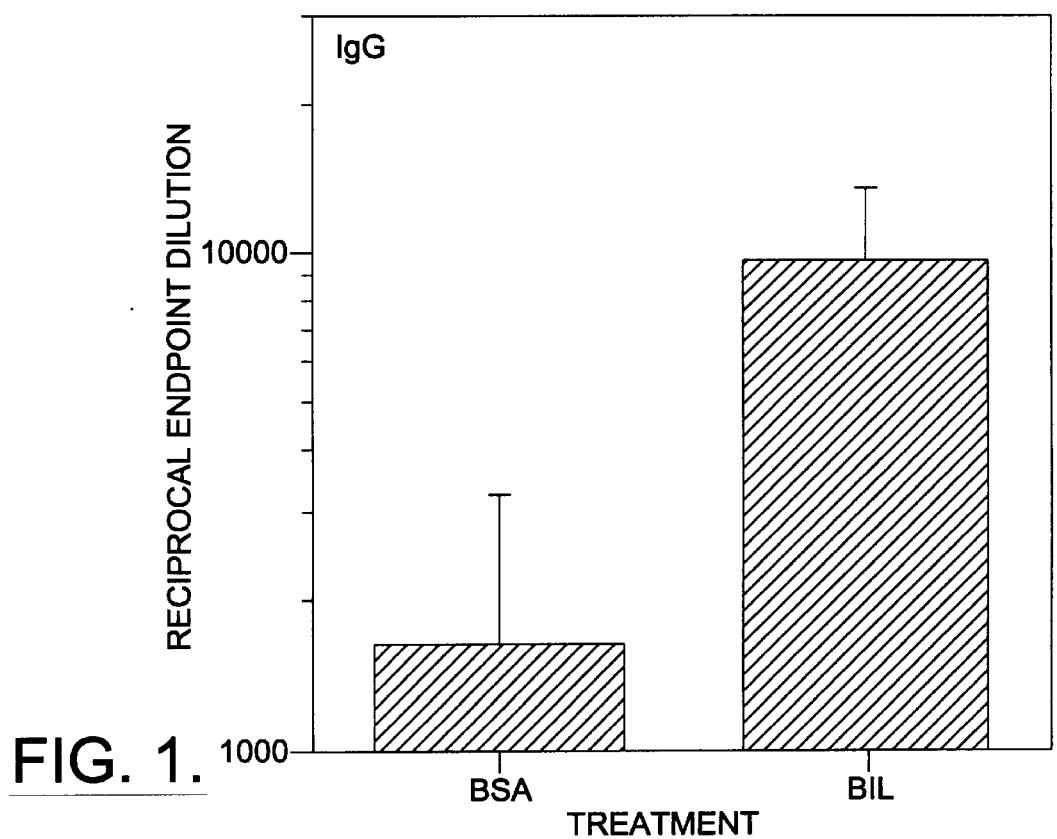

United States Patent [19]
Alexander et al.

[11] Patent Number: 5,876,721
[45] Date of Patent: Mar. 2, 1999

[54] VACCINES

[75] Inventors: James Alexander, Bearsden; James MacDonald Brewer, Hyndland, both of United Kingdom

[73] Assignees: Proteus Molecular Design Limited, United Kingdom; The University of Strathclyde, Great Britain

[21] Appl. No.: 624,606

[22] PCT Filed: Oct. 5, 1994

[86] PCT No.: PCT/GB94/02169

§ 371 Date: May 8, 1996

§ 102(e) Date: May 8, 1996

[87] PCT Pub. No.: WO95/09651

PCT Pub. Date: Apr. 13, 1995

[30] Foreign Application Priority Data

Oct. 6, 1993 [GB] United Kingdom .................... 9320597

[51] Int. Cl.$^6$ .......................... A61K 39/00; A61K 9/127; A01N 25/26; A01N 37/18
[52] U.S. Cl. ..................................... 424/184.1; 424/278.1; 424/450; 424/198.1; 424/277.1; 424/417; 514/2; 514/955
[58] Field of Search .............................. 424/184.1, 278.1, 424/450, 198.1, 277.1, 417; 514/2, 955

[56] References Cited

U.S. PATENT DOCUMENTS

| | | |
|---|---|---|
| 4,578,269 | 3/1986 | Morein . |
| 4,772,471 | 9/1988 | Vanlerberghe et al. . |
| 5,019,384 | 5/1991 | Gefter et al. . |
| 5,156,766 | 10/1992 | Behan et al. . |
| 5,171,577 | 12/1992 | Griat et al. . |
| 5,604,256 | 2/1997 | Kogen et al. . |
| 5,679,355 | 10/1997 | Alexander et al. . |
| 5,716,611 | 2/1998 | Oshlack et al. . |

FOREIGN PATENT DOCUMENTS

| | | |
|---|---|---|
| 0433242 A1 | 6/1991 | European Pat. Off. . |
| 2189457 | 10/1987 | United Kingdom . |
| 8702250 A1 | 4/1987 | WIPO . |
| 9217179 | 10/1992 | WIPO . |
| 93/19781 | 10/1993 | WIPO . |

OTHER PUBLICATIONS

Chemical Abstract, vol. 121, No. 9, Issued Aug. 29, 1994, J.M. Brewer and J. Alexander, "Studies on the adjuvant activity of non–ionic surfactant vesicles: adjuvant–driven IgG2a production independent of MHC control", p. 815, No. 106161k.

Full article of the above abstract—"Studies on the adjuvant activity of non–ionic surfactant vesicles; adjuvant–driven IgG2a production independent of MHC Control", J.M. Brewer and J. Alexander, Vaccine 1994 vol. 12, No. 7, pp. 613–619.

Alexander et al, NATO ASI Series vol. H78 Toxoplasmosis; Ed. Smith pp. 217–229, Springer–Verlag, 1993.

Bülow et al, J. Immunology, 147(10):3496–3500, 1991.

Eppstein et al, CRC Critical Rev. in Therapeutic Drug Carrier Systems. 5(2):99–139, 1988.

Langer Science 249:1527–1533, 1990.

Brewer et al, Immunology 75:570–575, 1992.

Devlin, Textbook of Biochemistry With Clinical Correlations 3$^{rd}$ Edition pp. 213–214, 438–447, 1082–1089:Wiley–Liss, 1992.

Edelman et al, Intern. Rev. Immunol 7:51–66, 1990.

Florence, Liposome Technology 2$^{nd}$ Edition, Ed. Gregoriadis. pp. 157–176. CRC Press, 1993.

Bomford, Rev. in Med. Virol, 2:169–174, 1992.

Bennett et al, J. Immunol Methods 153:31–40, 1992.

Walker et al, Eur. J. Immunol, 25:1426–1430, 1995.

Roberts et al. Vaccine, 12(15): 1389–1394, 1994.

Walker et al, Eur. J. Immunol; 26: 1664–1667, 1996.

Baillie et al, J. Pharm. Pharmacol., 37:863–868, 1985.

*Primary Examiner*—Nita Minnifield
*Attorney, Agent, or Firm*—Bell Seltzer Intellectual Property Law Group of Alston & Bird LLP

[57] ABSTRACT

Vesicles comprising at least one non-ionic surfactant and at least one molecule having the ability to transport or facilitate the transport of fats, fatty acids and lipids across mucosal membranes. With entrapped antigen they can act as immunological adjuvants. Vaccines based therein are active orally as well as by conventional administration routes and are simulators of antibody production via the Th 1 T lymphocyte partway.

32 Claims, 3 Drawing Sheets

VACCINES

The present invention relates to vehicles having novel compositions and to their use as an adjuvant, particularly for orally administered vaccines as well as to vaccines administered by the conventional parenteral route.

Vehicles composed of various types of amphipathic molecules are known. These include liposomes, which have a phospholipid bilayer, and non-ionic surfactant vesicles (NISV), in which the vesicles are formed essentially of non-ionic surfactants (NIS) such as polyoxyethylene aliphatic ethers. Both types of vesicle have an aqueous compartment enclosed by the bilayer or lamella within which various molecules can be entrapped as solutes.

Vesicles comprising a phospholipid bilayer occur naturally and are important in biological systems, eg. as microsomes. Non-ionic surfactant vesicles (NISV) are used in the cosmetic field e.g. as moisturising agents.

By virtue of the ability to entrap or encapsulate molecules, these vesicles are used in the medical field as carriers, e.g. for drug delivery.

As is described in our international patent application no. PCT/GB93/00716 filed 6th Apr. 1993, non-ionic surfactant vesicles containing entrapped antigens act as potent immunological adjuvants.

We have now found that a new type of vesicle structure comprising non-ionic surfactants together with molecules having the ability to transport, or facilitate the transport of, fats, fatty acids, and lipids across mucosal membranes (hereinafter termed "transport enhancers") are capable, when an antigen is entrapped therein, of acting as potent immunological adjuvants, the adjuvant effect being particularly striking with vaccines of this type administered orally.

Thus according to one aspect the present invention provides at least one antigen entrapped in vesicles comprising at least one non-ionic surfactant and at least one molecule having the ability to transport, or facilitate the transport of, fats, fatty acids and lipids across mucosal membranes.

According to a further aspect, we provide a composition comprising vesicles with entrapped antigen according to the invention together with a pharmaceutically acceptable carrier or excipient. In a preferred aspect, the composition is in a form suitable for oral administration.

Adjuvants are agents which assist in stimulating the immune response, a property which is highly desirable for certain antigens, notably those of low molecular weight such as peptides, which are inherently weak stimulators of the immune system even when coupled to carriers.

Although the use of adjuvants can overcome these problems, many adjuvants introduce further difficulties. The only adjuvant currently licensed for use in man is aluminium hydroxide. However, aluminium hydroxide is not considered to be an adequate adjuvant for all antigens as it does not adequately boost cell-mediated immunity (CMI), an essential property if a vaccine is to be successful, especially against intracellular pathogens such as Leishmania, Toxoplasma and viruses. Freund's Complete Adjuvant (FCA) does stimulate cellular immunity but is unsuitable for human or veterinary use as it promotes granuloma formation, adhesions, and other toxic side effects. FCA also produces a local inflammatory reaction which can persist for months. There is an urgent need for new non-toxic adjuvants which promote cell-mediated immunity. Indeed, such adjuvants will be essential if the full potential of vaccines based on peptide antigens is to be realised. This need is met at least to a major extent by the adjuvants of the present invention/

Thus according to another aspect, the present invention provides a vaccine comprising at least one antigen entrapped in vesicles comprising at least one non-ionic surfactant and at leas one molecule having the ability to transport, or facilitate the transport of, fats, fatty acids and lipids across mucosal membranes.

According to another aspect, the present invention provides a method of potentiating the immunological response to at least one antigen in a mammalian or non-mammalian subject which comprises administering said at least one antigen entrapped in vesicles comprising at least one non-ionic surfactant and at least one molecule having the ability to transport, or facilitate the transport of, fats, fatty aids and lipids across mucosal membranes.

According to a yet further aspect, the present invention comprises a method for preparing a vaccine comprising entrapping at lease one antigen in vesicles comprising at least one non-ionic surfactant and at least one molecule having the ability to transport, or facilitate the transport of, fats, fatty acids and lipids across mucosal membranes.

In these aspects of the present invention, the vesicular components are, of course, desirably pharmacologically acceptable.

The adjuvants of the present invention are suitable for varied types of antigen, including peptide antigens such as synthetic peptide antigens which notoriously are only weak stimulators of the immune system and also for potentiated forms thereof such as subunit vaccines which contain only certain antigenic parts of the pathogen. The adjuvants of the present invention can also be used for antigens which are inherently capable of acting as vaccines and those formulated with effective adjuvants whose properties may be augmented.

We have found that the adjuvant effect is generally at least equivalent to that achieved with vesicles comprised of non-ionic surfactant alone, as described in our PCT/GB93/00716, and sometimes greater, particularly when orally administered.

A variety of molecules which have the transporting characteristics required for the vesicles of the present invention may be used, however cholesterol derivatives in which the $C^{23}$ carbon atom of the side chain carries a carboxylic acid, and derivatives thereof are particularly preferred.

Amongst such derivatives are the "bile acids" cholic acid and chenodeoxycholic acid, their conjugation products with glycine or taurine such as glycocholic and taurocholic acid, and derivatives including deoxycholic and ursodeoxycholic acid, and salts of each of these acids; vesicles comprising these molecules constitute a particularly preferred aspect of the invention.

Although "bile salts" are known as penetration enhancers to aid the mucosal administration of drugs, and particularly for protein or peptide drugs which are nasally administered, they have never previously been incorporated into vesicles, nor have they been utilised for potentiating the immune response to orally administered substances. Indeed, the detergent properties of "bile salts" might be expected to have a disruptive effect on the integrity of vesicles.

Also preferred as transport enhancers of the present invention are acyloxylated amino acids, preferably acyl carnitines and salts thereof particularly those containing $C_{6-20}$ alkanoyl or alkenoyl moieties, such as palmitoyl carnitine. Again, these compounds have not previously been incorporated into non-ionic surfactant vesicles. As used herein, the term acyloxylated amino acid is intended to cover primary, secondary and tertiary amino acids as well as α, β, & γ amino acids. Acylcarnitines are examples of acyloxylated γ amino acids.

The vesicles of the invention may comprise more than one type of transport enhancer in addition to the non-ionic surfactants for example one (or more) different bile salts and one (or more) acylcarnitines.

The non-ionic surfactant used to form the vesicles of the invention may be any material with the appropriate surface active properties. However, in forming the basis of vesicles to act as immunological adjuvants in conjunction with an antigen it is of course desirable that the surfactant is pharmacologically acceptable. Preferred examples of such materials are ester linked surfactants based on glycerol. Such glycerol esters may comprise one of two higher aliphatic acyl groups e.g. containing at least ten carbon atoms in each acyl moiety. Surfactants based on such glycerol esters may comprise more than one glycerol unit, preferably up to 5 glycerol units and more preferably 4 glycerol units. Glycerol monoesters are preferred, particularly those containing a $C_{12}$–$C_{20}$ alkanoyl or alkenoyl moiety, for example caproyl, lauroyl, myristoyl, palmitoyl, oleyl or stearoyl. A particularly preferred surfactant is 1-monopalmitoyl glycerol.

Ether-linked surfactants may also be used as the non-ionic surfactant of which the vesicles according to the invention are comprised. Preferred examples of such materials are ether-linked surfactants based on glycerol or a glycol preferably a lower aliphatic glycol of up to 4 carbon atoms, most preferably ethylene glycol. Surfactants based on such glycols may comprise more than one glycol unit, preferably up to 5 glycol units and more preferably 2 or 3 glycol units, for example diglycol cetyl ether or polyoxyethylene-3-lauryl ether. Glycol or glycerol monoethers are preferred, particularly those containing a $C_{12}$–$C_{20}$ alkanyl or alkenyl moiety, for example capryl, lauryl, myristyl, cetyl, oleyl or stearyl.

The ethylene oxide condensation products usable in this invention include those disclosed in WO88/06882, i.e. polyoxyethylene higher aliphataic ether and amine surfactants. Particularly preferred ether-linked surfactants are 1-monocetyl glycerol ether and diglycol cetyl ether. However, for use in the adjuvant aspect of the present invention it is necessary to select pharmacologically acceptable materials, preferably those which are readily biodegradable in the mammalian system. For this reason, we prefer the aforementioned glycerol esters for preparing vesicles to be administered by injection, either subcutaneous, intramuscular, intradermal or intraperitoneal, or via the mucosal route such as by oral, nasal, bronchial, urogenital or rectal administration, oral administration being particularly preferred.

For effective vesicle formation, it is desirable that the vesicle components are admixed with an appropriate hydrophobic material of higher molecular mass capable of forming a bi-layer, particularly a steroid, e.g. a sterol such as cholesterol. The presence of the steroid assists in forming the bi-layer on which the physical properties of the vesicle depend.

The vesicles according to the invention may also incorporate a charge-producing amphiphile, to cause the vesicles to take on a negative charge. This helps to stabilise the vesicles and provide effective dispersion. Acidic materials such as higher alkanoic and alkenoic acids (e.g. palmitic acid, oleic acid); or other compounds containing acidic groups, e.g. phosphates such as dialkyl, preferably di(higher alkyl), phosphates, e.g. dicetyl phospate, or phosphatidic acid or phosphatidyl serine; or sulphate monoesters such as higher alkyl sulphates, e.g. cetyl sulphate, may all be used for this purpose.

In the vesicles of the present invention the transport enhancer may eg. comprise up to 2000% by weight of the non-ionic surfactant, preferably 40 to 400 percent. The steroid if present may e.g. comprise 20–120 percent by weight of the non-ionic surfactant, preferably 60–100 percent. The amphiphilic material producing a negative charge may e.g. comprise 1–30 percent by weight of the non-ionic surfactant.

The vesicles according to the present invention may be made by modifications of known techniques for preparing vesicles comprising non-ionic surfactants, such as those referred to in our pending international patent application no. PCT/GB93/00716. A preferred technique is the rotary film evaporation method in which a film or non-ionic surfactant is prepared by rotary evaporation from an organic solvent e.g. a hydrocarbon or chlorinated hydrocarbon solvent such as chloroform (Russell and Alexander, J Immunol 140 1274 (1988)). The resulting thin film is then rehydrated in bicarbonate buffer in the presence of the transport enhancer.

Another preferred method for the production of the vesicles of the invention is that disclosed by Collins et al. J. Pharm. Pharmacol 42, 53 (1990). This involves melting a mixture of the non-ionic surfactant, steroid (if used) and amphiphile and hydrating with vigorous mixing in the presence of aqueous buffer. The transporter molecule can be incorporated into the vesicles either by being included with the other constituents in the melted mixture or concomittantly during the process used to entrap the antigen as described herein.

The non-ionic surfactant and other membrane-forming material may also be converted to the vesicles of the invention by hydration in the presence of shearing forces. Apparatus to apply such shearing forces is well known, suitable equipment being mentioned e.g. in WO88/06882. Sonication and ultra-sonication are also effective means to form the vesicles or to alter their particle size.

To form the vaccines of the invention, antigen must be enclosed or entrapped in the vesicles. In the preferred rotary film evaporation technique, this is achieved by hydration of the film in the presence of antigen together with the transporter molecule.

In other methods, antigens may be entrapped within preformed vesicles by the dehydration-rehydration method (Kirby & Gregoriadis, Biotechnology 2 979 (1984) in which antigen present in the aqueous phase is entrapped by flash freezing followed by lyophilisation, or the freeze thaw technique (Pick. Arch. Biochem. Biophys. 212 195 (1981)). In the latter technique, vesicles are mixed with antigen and repeatedly flash frozen in liquid nitrogen and e.g. warmed to temperature of the order of 60° C. (i.e. above the transition temperature of the relevant surfactant). In addition to entrapping the antigen, the dehydration-rehydration method and freeze-thaw technique are also capable of concomittantly incorporating the transporter molecule into the vesicles. Where this approach is adopted for incorporation of the transporter molecule into the vesicles, the freeze thaw technique is preferred.

The vesicles may be further processed to remove any non-entrapped antigen e.g. by washing and centrifuging. It should be noted that our results clearly show that the non-ionic surfactant alone is not an effective adjuvant, i.e. vesicular formation is essential to obtain the desired effect. The antigen must be entrapped within the vesicles if the desired adjuvant effect is to be achieved.

In each of these methods, the suspension of vesicle components may be extruded several times through microporous polycarbonate membranes at an elevated temperature sufficient to maintain the vesicle-forming mixture in a molten condition. This has the advantage that vesicles having a uniform size may be produced.

Vesicles for forming the basis of vaccines according to the invention may be of diameter 10 nm to 5 µm, preferably 100 nm to 1 µm.

The vaccines of the present invention are suitable for use with many types of antigen, including peptide antigens. It is now possible to produce synthetic antigens which mimic the antigenically significant epitopes of a natural antigen by either chemical synthesis or recombinant DNA technology. These have the advantage over prior vaccines such as those based on attenuated pathogens of purity, stability, specificity and lack of pathogenic properties which in some cases can cause serious reaction in the immunised subject. The vesicles of the invention may be used with any form of antigen, including those inherently capable of acting as vaccines and those which are formulated with effective adjuvants.

Preferred peptides of synthetic or recombinant origin contain e.g. from 8–50, preferably from 10–20 amino acid units. The antigen may e.g. mimic one or more B cell, or B cell and T cell epitopes of a patogenic organism, so that the vaccine elicits both neutralising antibodies and a T cell response against the organism (see, for example, the disclosure of synthetic antigens to MIV in our WO88/10267 and WO97/13909).

Alternatively, the peptide may elicit an immune response against another biologically active substance, particularly a substance having hormonal activity. An example in the latter category would be the induction of an immune response against endogenous luteinising hormone-releasing hormone (LHRH). Such treatment can e.g. be used for suppression of sex steroid hormone levels for the treatment of androgen- and oestrogen-dependent carcinomas and in the immunocastration of farm and domestic animals (see our GB-B-2196969).

In some cases it may be desirable to link the peptide to a carrier to boost its immunogenicity. Suitable carriers are well known in the art, e.g. protein carriers such as purified protein derivative of tuberculin (PPD), tetanus toxoid, cholera toxin and its B subunit, ovalbumin, bovine serum albumin, soybean trypsin inhibitor, muramyl dipeptide and analogues thereof, and a cytokine or fraction thereof. When using PPD as the carrier, a higher titre of antibodies is achieved if the recipient of the vaccine is already tuberculin sensitive, e.g. by virtue of earlier BCG vaccination.

The antigen(s) entrapped in the vesicles of the invention may be formulated into a vaccine using conventional methods of pharmacy, such as by suspension in a sterile parenterally-acceptable aqueous vehicle. The non-ionic surfactant vesicles with antigen entrapped may also be freeze-dried and stored.

Although synthetic or recombinant peptides are the preferred antigens for use in this invention, a strong adjuvant effect is also observed when protein antigens are entrapped in the vesicles of the invention. For example, strongly positive results have been obtained using bovine serum albumin (BSA) as the antigen.

We have found that the vaccines of the present invention are particularly effective when administered orally, particularly for the stimulation of a cell-mediated response, although antibody levels are also amplified. Other conventional modes of administration are however possible including injection, both subcutaneous, intramuscular or intraperitoneal, and via other mucosal routes such as the nasal, bronchial, urogenital or rectal routes.

Our invention therefore provides a method of formulating an antigen as an orally-active vaccine which comprises entrapping said antigen in vesicles comprising at least one non-ionic surfactant and at least one molecule having the ability to transport, or facilitate the transport of, fats, fatty acids and lipids across mucosal membranes.

The ability to achieve an adjuvant effect by oral administration e.g. of a synthetic peptide is a highly beneficial property of the vaccines of the present invention, and is a property th whilst being previously contemplated in the prior art has not yet been realised. The oral administration route has several advantages over the previous administration routes of injection. Dangers of infection which accompany injection such as, for example, derive from the use of non-sterile needles, are avoided. In addition to inducing a systemic immune response, oral administration may also induce a mucosal response. Such a mucosal response is thought to be important in immunological protection against many pathogens, e.g. HIV, Toxoplasma. Acceptability to patients is also higher for oral compositions. Hence greater levels of vaccination within the population may be achievable as compared to traditional parenteral vaccine regimes.

In formulating vesicles to be used as vaccines specifically to be orally administered, ester-linked surfactants are preferred, although ether-linked surfactants particularly 1-monocetyl glycerol ether and diglycol cetyl ether may be used.

We have found that oral vaccines according to the present invention not only are capable of stimulating antibody production i.e. a systemic immune response but can also lead to antibody production upon a second challenge in cases where a less significant response is achieved on first challenge. The vesicles of the invention are also capable with entrapped antigen of priming the immune system for antibody production upon subsequent challenge particularly when orally administered. This makes the vesicles with entrapped antigen highly suitable as vaccines.

Further analysis of the immune response produced by the novel vaccine of the invention has shown that the level of IgG2a antibodies elicited when compared to immunisation with BSA alone is markedly higher, reaching a 10 to 20 fold difference. High levels of IgG2a are believed to be associated with the production of interferon-γ from Th1 cells which mediate the development of cell-mediated immunity. Thus the vesicles of the present invention appear to be ideally suited for use as vaccines requiring stimulation of this facet of the immune response.

An advantage of the vesicles of the invention as adjuvants is their stability and substantial non-toxicity. The vaccines contemplated by this invention are primarily applicable to mammals and are thus useful in both human and veterinary medicine. It is also envisaged that the vesicles of the invention can provide an effective adjuvant for non-mammalian species e.g. fish and poultry.

The vesicles and adjuvant properties thereof are illustrated in the following non-limiting Examples.

EXAMPLE 1

Preparation of vesicles containing Ox Bile by Rotary Film Evaporation

Vesicles were formed from 1-monopalmitoyl glycerol ester (MPG) in the molar ration 5:4:1 MPG:cholesterol:dicetyl phosphate (i.e. 24.8 mg:23.2 mg:8.2 mg). Vesicles were prepared by rotary film evaporation from chloroform as described by Russell land Alexander (Supra). The 150 µmoles of surfactant formed into thin film was hydrated in 5 ml of carbonate buffer containing 100 mg of BSA-100 mg ox bile (Sigma). The mixture was shaken for 2 hours at 60°

C., sonicated for 5 minutes in a water-bath sonicator at 60° C. and then incubated for 2 hours in a shaking water bath. Non-entrapped antigen was removed by twice washing with carbonate buffer and centrifuging at 100000 g for 40 minutes. The presence of bile acids in the washed vesicle preparations was confirmed by this layer chromatography.

The ox bile used is dried ox gall powder. This essentially consists of bile acids, e.g. cholic acid, deoxycholic acid and taurocholic acid.

The same procedure was used for the preparation of vesicles containing individual bile acids.

EXAMPLE 2

Preparation of Vesicles Containing Palmitoyl Carnitine

Vesicles are prepared by the technique described in Example 1 execpt that 100 mg palmitoyl carnitine replaces ox bile in the hydration step.

EXAMPLE 3

Preparation of Vesicles Containing Ox Bile or palmitoyl Carnitine by Freeze Thaw Vesicles were formed from 1-monopalmitoyl glycerol ester (MPG) in the molar ration 5:4:1 MPG:cholesterol:diectyl phosphate (i.e. 24.8 mg:23.2 mg:8.2 mg). Vesicles were prepared using the melt method as described by Collins et al. (Supra) and incubated in a shaking water bath for 2 hours at 60° C. Antigen was entrapped into the preformed vesicles and palmitoyl carnitine or bile (ox gall or individual bile acid salts) concomitantly incorporated in the lamella of the vesicles using the freeze-thaw technique as described by Pick (Supra). 2.5 ml (75 μmoles) of vesicles in carbonate buffer (pH 9.4) were mixed with 5 mg of palmitoyl carnitine (Sigma) or 20 mg of bile. The mixture was flash frozen in liquid nitrogen and thawed to 60° C. This was repeated 5 times. The vesicles were twice washed by centrifugation at 100,000 g for 40 minutes using carbonate buffer. The presence of palmitoyl carnitine or bile in the washed vesicle preparations was confirmed by thin layer chromatography.

EXAMPLE 4

Oral Immunisation of Mice with BSA Entrapped in Vesicles

Vesicles comprising ox bile were prepared in accordance with the procedure of Example 1. Vesicles were similarly prepared but omitting the ox bile.

8–10 week old female BALR/c mice were used with five mice in each treatment group. Each group received one of the following.
a) BSA in carbonate buffer
  b) BSA in MPT NISV prepared in the presence of 20 mg/ml ox bile.

The mice received a primary oral dose of 0.1 ml (240 μg BSA per mouse) administered by gavage tube on day 1. On day 12, a secondary oral dose was administered (500 μg BSA per mouse). Blood samples were collected on days 20 and 24 and analysed for anti-BSA IgG titre by Elisa (Brewer and Alexander, Immunology 75, 570–575 (1992)).

Figure 2:
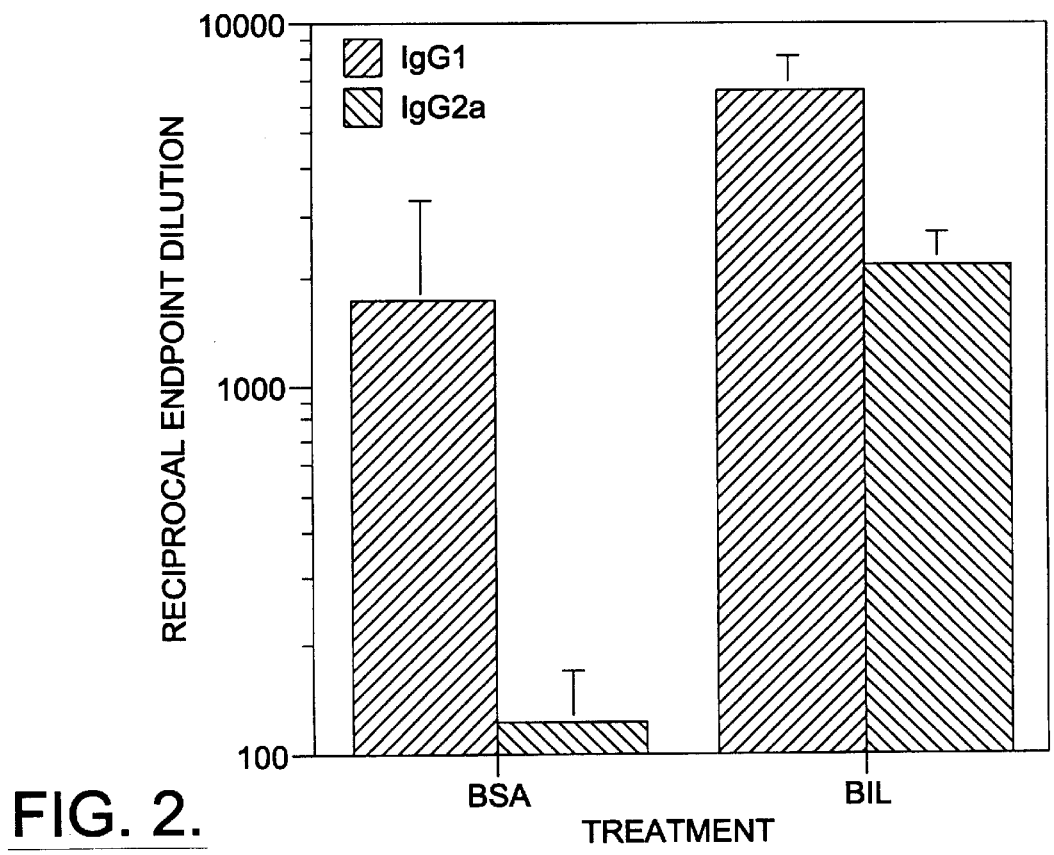

The IgG responses for the two bleeds at 8 and 12 days after the last inoculation were very similarly and the data for 12 day bleeds is presented in FIGS. 1 and 2. FIG. 1 shows the total serum IgG titres obtained. It can clearly be seen that BSA entrapped in vesicles containing bile salts induced a greatly increased IgG response as compared to that elicited by BSA alone (p<0.05).

FIG. 2 shows an isotype analysis of the antibody response. Whilst in absolute terms BSA in vesicles containing ox bile produced a higher IgG1 response than BSA alone (approx 3 fold) the IgG2a response elicted was some 10–20 fold higher than that achieved with BSA alone. This strongly suggests that a cell-mediated response has been induced.

EXAMPLE 5

Recall Response of Mice Orally Immunised with BSA Entrapped within Vesicles Vesicles were formed from 1-monopalmitoyl glycerol ester (MPG) as described in Example 1. The 150 μmoles of surfactant formed into thin film was hydrated in 5 ml of carbonate buffer containing one of the following: 100 mg of BSA, 100 mg of BSA+100 mg ox bile (Sigma), or, 100 mg BSA +100 mg of deoxycholate (DOC) (Sigma). The mixture was shaken for 2 hours at 60° C.

8–10 week old female BALB/c mice were used with five mice in each treatment group. Each group received one of the following.
  a) BSA in carbonate buffer
  b) BSA in MPG NISV prepared in the presence of 20 mg/ml ox bile
  c) BSA in MPG NISV prepared in the presence of 20 mg/ml DOC.

Figure 3:
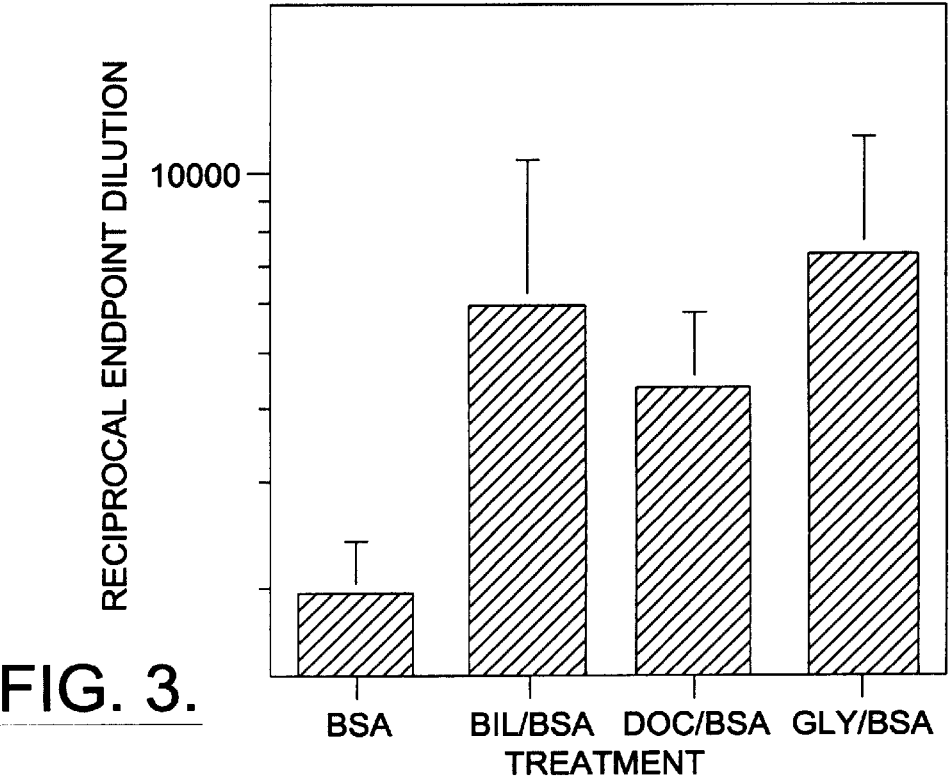

The mice received a primary oral dose of 0.1 ml (240 μg BSA per mouse) administered by gavage tube on day 1. A secondary oral dose (500 μg BSA per mouse) was administered at two weeks. After 4 weeks, each mouse was challenged with a subcutaneous injection of BSA (100 μg in PBS). Blood samples were collected two weeks after the BSA challenge and analysed for anti-BSA IgG titre by ELISA. The mean values from each treatment group were recorded in FIG. 3.

Mice which received two doses of antigen incorporated into vesicles produced a much greater serum IgG response to BSA when challenged systemically than those animals in the control group. The highest titres were obtained with vesicles containing bile salts, either individually or as oxbile, in addition to non-ionic surfactants These results suggest that the presence of bile salts in the vesicle formulation improves the priming effect (i.e. the generation of a memory pool of antigen-specific immune cells) of the vesicles.

EXAMPLE 6

Recall Response of Mice Orally Immunised with BSA Entrapped in Vesicles Prepared with Individual Bile Acids Vesicles were formed from 1-monopalmitoyl glycerol ester as in Example 5. 150 μmoles of surfactant formed into thin film were hydrated in 5 ml of carbonate buffer containing 100 mg BSA+100 mg glycocholic acid (Gly) (Sigma) as in Example 5. The vesicles were administered to mice and blood samples taken for analysis according to Example 5 and the data is presented in FIG. 3.

EXAMPLE 7

Effect of Number of Oral Doses of BSA entrapped in Vesicles on Serum Antibody Response The purpose of this experiment was to examine if the number of oral doses had nay effect on the subsequent ability of antigen formulations to induce the production of specific IgG.

Vesicles were formed from 1-monopalmitoyl glycerol ester (MPG) by rotary film evaporation as described in Example 1, 8–10 week old female BALB/c mice were used with three mice in each treatment group. Each group received one of the following.

a) BSA in carbonate buffer (A1–A3)
b) BSA in MPG NISV prepared in the presence of 20 mg/ml ox bile (B1–B3)

Figure 4:
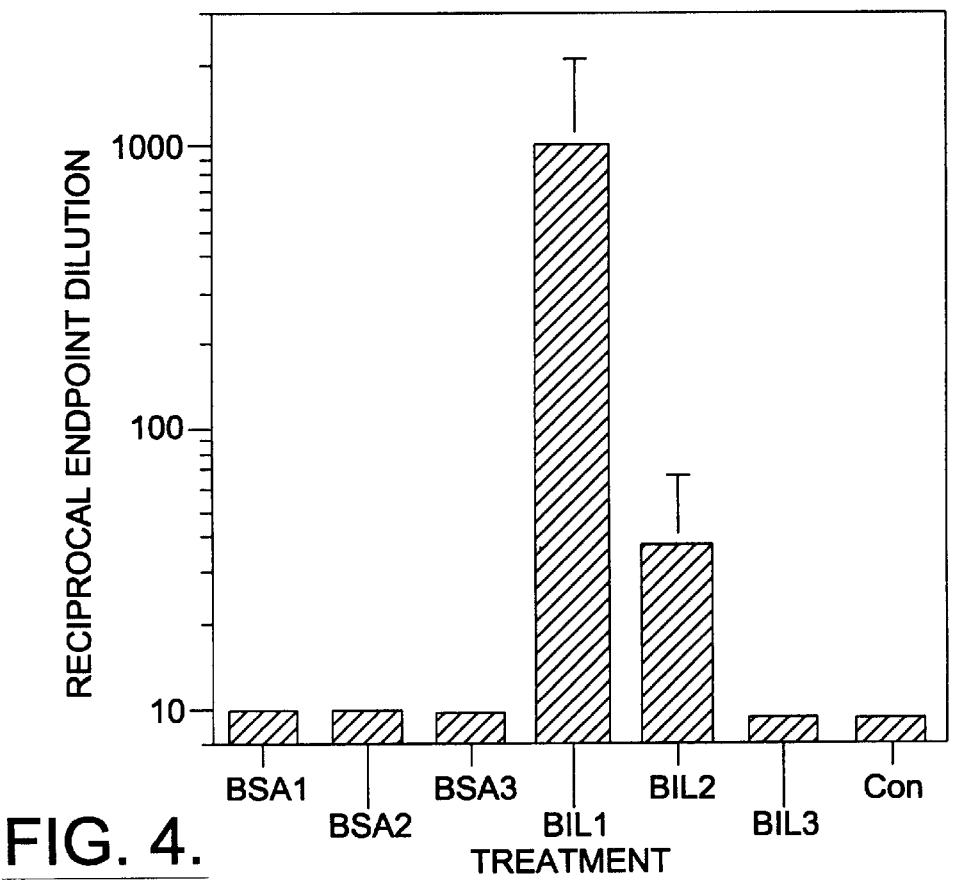

This mice received one, two or three oral doses of 0.2 ml (500 µg BSA per mouse) administered by gavage tube over a one week period. Those mice who received a single dose received it on day 1, those who received two doses received them on days 1 and 4, and those who received three doses received them on days 1, 4 and 7. The immunisation regime was repeated two weeks later and blood samples collected another 2 weeks thereafter. The BSA-specific IgG response at this time point is shown in FIG. 4.

As would be expected for oral administration of a simple protein antigen, no IgG production could be detected in those animals dosed with antigen in carbonate (ie without vesicles) regardless of frequency of dosing (A1–A3), While one of the three mice responded after two repeated single doses of NISV/bile (B1), increasing the frequency of dosing two repeated doses twice in a week (B2) had no effect on the response and two repeated doses three times a week produced no responders at all (B3).

Figure 5:
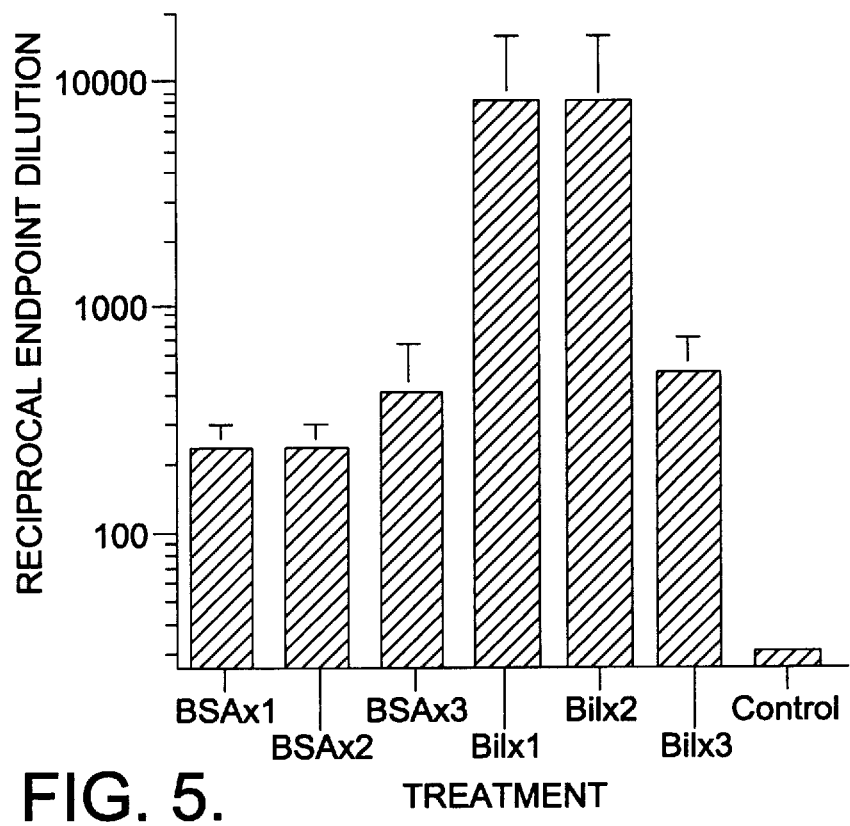

The immunisation regime was repeated for a third time but little change was observed in this pattern of response. Two weeks later, each mouse was challenged with a subcutaneous injection of 100 µg BSA in PBS. Two weeks after challenge, a recall serum IgG response was observed in all groups as shown in the results of FIG. 5. However, a higher antibody production was observed in mice orally dosed once or twice with antigen entrapped within NISV/bile than with antigen alone.

Thus the vesicles of the invention with entrapped antigen are particularly effective at eliciting a serum antibody response with a low number of oral doses.

We claim:

1. A non-ionic surfactant vesicle comprising:
   at least one non-ionic surfactant; and
   at least one compound selected from the group consisting of:
   (i) cholesterol derivatives in which the C23 carbon atom of the side chain carries a carboxylic acid;
   (ii) derivatives of (i) selected from the group consisting of bile acids and conjugation products of bile acids with glycine or taurine;
   (iii) acyloxylated amino acids; and
   (iv) salts of (i), (ii), and (iii).

2. A non-ionic surfactant vesicle of claim 1, wherein said vesicle comprises from about 60 to about 100 percent of said compound by weight of said non-ionic surfactant.

3. A non-ionic surfactant vesicle of claim 1, wherein said (ii) derivatives of (i) comprise a compound selected from the group consisting of cholic acid, chenodeoxycholic acid, glycocholic acid, taurocholic acid, deoxycholic acid, and ursodeoxycholic acid.

4. A non-ionic surfactant vesicle of claim 1, wherein said (iii) acyloxylated amino acids comprise an acylcarnitine.

5. A non-ionic surfactant vesicle of claim 4, wherein said acylcarnitine is palmitoyl carnitine.

6. A non-ionic surfactant vesicle comprising:
   at least one non-ionic surfactant; and
   at least one compound selected from the group consisting of bile acids, conjugation products of bile acids with glycine or taurine, acyloxylated amino acids, and salts thereof.

7. A product comprising at least one antigen entrapped in vesicles, said vesicles comprising:
   at least one non-ionic surfactant; and
   at least one compound selected from the group consisting of:
   (i) a cholesterol derivative in which C23 carbon atom of the side chain carries a carboxylic acid;
   (ii) derivatives of (i), selected from the group consisting of bile acids and conjugation products of bile acids with glycine or taurine;
   (ii) acyloxylated amino acids; and
   (iv) salts of (i), (ii), and (iii).

8. A product of claim 7, wherein said (ii) derivatives of (i) comprise a compound selected from the group consisting of cholic acid, chenodeoxycholic acid, glycocholic acid, taurocholic acid, deoxycholic acid, and ursodeoxycholic acid.

9. A product of claim 7, wherein said (iii) acyloxylated amino acids comprise an acylcarnitine.

10. A product of claim 9, wherein said acylcarnitine is palmitoyl carnitine.

11. A product of claim 7, wherein the non-ionic surfactant is selected from the group consisting of (i) glycerol esters, (ii) ethers based on glycerol, and (iii) ethers based on a lower aliphatic glycol.

12. A product of claim 11, wherein the glycerol ester is a glycerol monoester comprising C12–C20 alkyanoyl or alkenoyl moieties.

13. A product of claim 12, wherein the glycerol ester is 1-monopalmitoyl glycerol.

14. A product of claim 11, wherein (ii) and (iii) are glycerol monoethers or monoethers based on lower aliphatic glycols comprising C12–C20 alkanyl or alkenyl moieties.

15. A vaccine comprising the product of claim 7.

16. A vaccine of claim 15, wherein said vaccine is in a form suitable for oral administration.

17. A pharmaceutical composition comprising the product of claim 7 and a pharmaceutically acceptable carrier or excipient.

18. A pharmaceutical composition of claim 17, wherein said composition is in a form suitable for oral administration.

19. A pharmaceutical composition of claim 17, wherein said composition is in the form of a powder, tablet, syrup, capsule or granule.

20. A method of making a vaccine in a vesicle, comprising entrapping at least one antigen in a vesicle comprising:
   at least one non-ionic surfactant; and
   at least one compound selected from the group consisting of:
   (i) a cholesterol derivative in which the C23 carbon atom of the side chain carries a carboxylic acid;
   (ii) derivatives of (i) selected from the group consisting of bile acids and conjugation products of bile acids with glycine or taurine;
   (iii) acyloxylated amino acids; and
   (iv) salts of (i), (ii), and (iii); and recovering said vesicle.

21. A method of making a vaccine of claim 20, wherein said antigen is entrapped within said vesicle by hydrating a non-ionic surfactant film prepared by rotary film evaporation in the presence of said antigen and said compound.

22. A method of making a vaccine of claim 20, wherein said antigen is entrapped within said vesicle by dehydration-rehydration.

23. A method of making a vaccine of claim 20, wherein said antigen is entrapped within said vesicle by freeze-thawing.

24. A method of stimulating the immune response to at least one antigen in a subject capable of immune response comprising:
  administering to a subject a vaccine comprising said antigen entrapped within a vesicle comprising at least one non-ionic surfactant and at least at least one compound selected from the group consisting of:
    (i) a cholesterol derivative in which the C23 carbon atom of the side chain carries a carboxylic acid;
    (ii) derivatives of (i) selected from the group consisting of bile acids and conjugation products of bile acids with glycine of taurine;
    (iii) acyloxylated amino acids; and
    (iv) salts of (i), (ii), and (iii).

25. A method of stimulating immune response of claim 24, wherein said subject is a mammal.

26. A method of stimulating immune response of claim 24, wherein said subject is human.

27. A method of stimulating immune response of claim 24, wherein the vaccine is administered orally.

28. A method of stimulating immune response of claim 24, wherein the vaccine is administered orally.

29. A method of stimulating cell-mediated immune response to al least one antigen in a subject capable of immune response, comprising:
  administering to a subject a vaccine comprising said antigen entrapped within a vesicle comprising at least one non-ionic surfactant and at least one compound selected from the group consisting of:
    (i) a cholesterol derivative in which the C23 carbon atom of the side chain carries a carboxylic acid;
    (ii) derivatives of (i) selected from the group consisting of bile acids and conjugation products of bile acids with glycine or taurine;
    (iii) acyloxylated amino acids; and
    (iv) salts of (i), (ii), and (iii).

30. A method of stimulating cell-mediated immune response of claim 29, wherein said vaccine is administered orally.

31. A method of stimulating the humoral immune response to at least one antigen in a subject capable of immune response, comprising:
  administering to a subject a vaccine comprising said antigen entrapped within a vesicle comprising at least one non-ionic surfactant and at least one compound selected from the group consisting of:
    (i) a cholesterol derivative in which the C23 carbon atom of the side chain carries a carboxylic acid;
    (ii) derivatives of (i) selected from the group consisting of bile acids and conjugation products of bile acids with glycine or taurine;
    (iii) acyloxylated amino acids; and
    (iv) salts of (i), (ii), and (iii).

32. A method of stimulating humoral immune response of claim 31, wherein said vaccine is administered orally.

* * * * *